United States Patent [19]

Behme et al.

[11] Patent Number: 4,810,789

[45] Date of Patent: Mar. 7, 1989

[54] PROCESS FOR BUSPIRONE HYDROCHLORIDE POLYMORPHIC CRYSTALLINE FORM CONVERSION

[75] Inventors: Robert J. Behme, Newburgh; Terry T. Kensler; Douglas G. Mikolasek, both of Evansville, all of Ind.

[73] Assignee: Bristol-Myers Company, New York, N.Y.

[21] Appl. No.: 90,302

[22] Filed: Aug. 28, 1987

[51] Int. Cl.$^4$ .......................................... C07D 401/14
[52] U.S. Cl. ................................................... 544/230
[58] Field of Search .......................................... 544/230

[56] References Cited

U.S. PATENT DOCUMENTS

| | | | |
|---|---|---|---|
| 3,717,634 | 2/1973 | Wu et al. | 544/230 |
| 3,976,776 | 8/1976 | Wu et al. | 514/252 |
| 4,351,939 | 9/1982 | Simms | 544/230 |
| 4,476,248 | 10/1984 | Gordon | 562/494 |

OTHER PUBLICATIONS

Wu, et al., *J. Med. Chem.*, 15, 477–479 (1972).
Allen, et al., *Arzneim. Forsch.*, 24, No. 6, 917–922 (1974).
Sathananthan et al., *Current Therapeutic Research*, 18/5, 701–705 (1975).

*Primary Examiner*—Donald G. Daus
*Assistant Examiner*—F. Bernhardt
*Attorney, Agent, or Firm*—Richard P. Ryan

[57] ABSTRACT

A process for conversion of one polymorphic crystalline form of buspirone into its other polymorphic crystalline form.

17 Claims, No Drawings

PROCESS FOR BUSPIRONE HYDROCHLORIDE POLYMORPHIC CRYSTALLINE FORM CONVERSION

FIELD OF THE INVENTION

This invention is concerned with a drug bioaffecting body-treating process which employs the pyrimidine compound 8-[4-[4-(2-pyrimidinyl)-1-piperazinyl]butyl]-8-azaspiro [4.5]decane-7,9-dione or a pharmaceutically acceptable acid addition salt thereof.

BACKGROUND OF THE INVENTION

The psychotropic compound with which the present invention is concerned has the following structural formula:

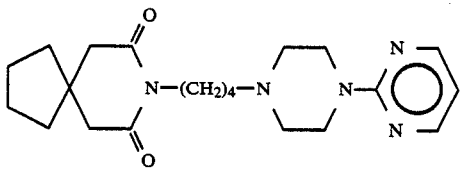

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN); refer to J. American Med. Assoc. 225, 520 (1973). Buspirone is currently approved for marketing as an effective clinical anti-anxiety agent.

The synthesis of the compound and the disclosure of its psychotropic properties are described in the following representative patents and publications.

1. Y. H. Wu. et al., J. Med. Chem., 15.477 (1972).
2. Y. H. Wu, et al., U.S. Pat. No. 3,717,634 which issued Feb. 20, 1973.
3. L. E. Allen et al., Arzneium. Forsch., 24. No. 6 917–922 (1974).
4. G. L. Sathananthan, et al., Current Therapeutic Research. 18/5, 701–705 (1975).
5. Y. H. Wu. et al., U.S. Pat. No. 3,976,776, issued Aug. 24, 1976.
6. J. C. Simms. U.S. Pat. No. 4,351,939, issued Sept. 28, 1982.

The melting point disclosed for buspirone hydrochloride in the above-listed references is 201.5° to 202.5° C. No other melting point values outside a range of 201° to 205° for pure buspirone hydrochloride has been previously disclosed. As one aspect of the instant invention it has been discovered that solid buspirone hydrochloride can exist in two different crystalline phases. The capacity to occur in different crystal structures is known as polymorphism and is known to occur in many organic compounds including drugs. These different crystalline forms are known as "polymorphic modifications" or "polymorphs" and are realized only in the crystalline state. While polymorphic modifications have the same chemical composition, they differ in packing, geometrical arrangement, and other descriptive properties of the crystalline solid state. As such, these modifications may have different solid-state physical properties such as shape, color, density, harness, deformability, stability, dissolution properties, and the like. Polymorphism of an organic drug molecule and its consequences would be appreciated by one skilled in the pharmaceutical arts.

As an example; Gordon, et al. in U.S. Pat. No. 4,476,248, issued Oct. 7, 1984, disclosed and claimed a new crystalline form of the drug ibuprofen as well as the process for producing it. The new crystalline form was reported to improve the manufacturability of ibuprofen.

In the manufacture of pharmaceutical supplies of buspirone hydrochloride, certain specified criteria, such as the melting point for example, defining physical characterization and purity of the pure drug substance must be met before it can be incorporated into pharmaceutical compositions for medicinal purposes. Satisfying these criteria is one requirement of the approvability process allowing continued distribution of drug product under good manufacturing procedure guidelines and regulations set forth by governmental agencies such as the Food and Drug Agency (FDA) in the U.S. Compliance with governmental regulations for drug manufacture requires meeting the requisite drug substance specifications as well as keeping related records and other quality assurance procedures for each batch of drug substance to be put into the pharmaceutical product manufacturing process. These requirements are required of every drug manufacturer for every drug falling under purview of the FDA or other appropriate governmental drug agency.

In the course of preparing larger batch lots of buspirone hydrochloride, a problem was experienced in meeting the specified melting point criterion. Closer examination led to the unexpected discovery of a second polymorphic modification of buspirone hydrochloride. This second polymorphic modification displays a melting point of about 188° as compared with the melting point of about 202° to 204° for the originally discovered polymorphic form. Since the extensive, expensive and time-consuming clinical studies required for drug approval were done with the original polymorph (designated P203), the specifications for drug substance are for this polymorph in the approved New Drug Application (NDA) of buspirone. However, increasing difficulty was experienced in continued preparation of P203 and, to add further complication, some batches of P203 underwent partial conversion to P188 during storage.

It is therefore an object of this invention to be able to reliably provide a crystalline form of buspirone hydrochloride which can be produced, stored, and compounded while continuing to meet its required specifications for a pure drug substance. It is a further object of this invention to provide a reliable process whereby whichever polymorphic form desired, P188 or P203, can be conveniently and reproducibly prepared.

Other objects, aspects and advantages of this invention will become apparent from reading the remaining specification and the claims which follow.

SUMMARY OF THE INVENTION

It has been found that buspirone hydrochloride can exist in two distinct polymorphic forms and when crystallized under equilibrium conditions at temperatures above about 95° C., the higher melting polymorphic modification is obtained and when crystallization proceeds under equilibrium conditions at temperatures below about 95° C., the lower melting polymorphic modification is obtained. It has also been found that the lower melting polymorph is the thermodynamically-favored form at pharmaceutically relevant temperatures. As a result of these discoveries, processes have been developed for the reliable production of either polymorphic modification of buspirone hydrochloride. In addition it has been found that the newly discovered lower melting polymorph provides a manufacturing advantage over the higher melting polymorph due to its retention of specified physical characteristics under pharmaceutically relevant storage and manufacturing conditions.

DETAILED DESCRIPTION OF THE INVENTION

Research carried out to investigate solid state behavior of the useful anxiolytic drug, buspirone hydrochloride, has resulted in the discovery that it can exist in the solid state in the form of two polymorphic modifications. Further it was discovered that the two polymorphic modifications of solid buspirone hydrochloride could exist in equilibrium with each other at a transition temperature of about 95° C. and that the lower-melting polymorph, P188, was thermodynamically favored at temperatures below and the higher-melting polymorph, P203, was favored at temperatures above this transition temperature. These discoveries have led to the development of useful, reliable processes which enable one to produce whichever polymorph one desires.

Previous methods of crystallizaton of buspirone hydrochloride generally employed alcoholic solvents, usually ethanol or isopropanol, and temperatures below 95° C. Under conditions of these methods, solid crystalline buspirone hydrochloride was forced from solution by chilling and the liberal use of P203 seed crystals. These conditions are understood to favor kinetic, or rate, control of product crystals and the high melting polymorph was usually produced with such methodology. With passage of time, use of such kinetic-controlled methods, where rate of crystallization favored the P203 polymorph, became less and less reliable and the resultant crystalline product was usually contaminated with the P188 polymorph. The problem that this other polymorph contamination causes is that an entire batch or lot of drug substance now does not meet the required physical specifications for incorporation into pharmaceutical products and must be re-worked. It is to be appreciated that considerable time and expense is involved in reworking large lots of buspirone hydrochloride in order to meet FDA specifications.

One aspect then of this invention is a process which reliably converts either one or a mixture of the two buspirone hydrochloride polymorphs into the other polymorph. In its most general form this process comprises the steps of:

(a) disrupting the crystalline structure of either one or a mixture of the two starting polymorphic forms of buspirone hydrochloride; and (b) allowing recrystallization to occur under equilibrium conditions at a temperature either higher than about 95° C. if the higher melting polymorphic crystalline form of buspirone hydrochloride is desired, or under equilibrium conditions at temperatures lower than about 95° C. if the lower melting polymorphic crystalline form of buspirone hydrochloride is desired.

Disruption of the crystalline structure encompasses processes ranging from crystal structure relaxation due to application of heat, to dissolution of the solid crystal by a suitable solvent, a combination of heat and dissolution, and even sublimation processes. Dissolution need only be partial, and in fact polymorph conversion can proceed under certain conditions of high humidity. In these humidity promoted polymorphic conversions, moisture-mediated dissolution-crystallization equilibrium is established and sorption processes, in particular capillary condensation, come into play. The strong influence of humidity on some polymorphic transformations is discussed by Ramberger, et al., *Ber. Bunsenges. Phys. Chem.* 84, 1261–1264 (1980).

Similarly, polymorphic conversions can be accomplished in solvents in which buspirone hydrochloride has only low solubility even at elevated temperatures. In these instances, usually selected for obtaining P203, the solid is heated above the transition temperature until conversion is complete and then the mixture is allowed to cool and the desired polymorph is isolated with negligible contamination.

Preferred processes of this invention are carried out in a liquid medium with agitation. The process temperature is selected according to the polymorph product desired and the liquid medium selected is generally one in which buspirone hydrochloride has some solubility.

A related aspect of the present invention deals with processes for the production of the low-melting polymorph of buspirone hydrochloride as well as processes for production of the high-melting polymorph. These processes are carried out preferably in liquid media in which the solid busipirone hydrochloride has some solubility. In general the processes involve the following steps:

(a) disrupting the crystal structure of solid buspirone hydrochloride by dissolution by the liquid medium:

(b) allowing recrystallization to occur in a selected temperature range, either above or below 95° C.:

(c) agitating the solid buspirone hydrochloride: liquid medium mixture for a time sufficient to obtain solid/solution equilibrium in the mixture; and (d) separating the desired crystalline polymorph from the liquid component of the mixture.

Disruption of the crystalline structure of solid buspirone hydrochloride by dissolution of the liquid medium encompasses a range of dissolution processes from complete dissolution to only slight dissolution. Degree of dissolution can be modified by selection of the appropriate liquid media and/or by selection of process temperature within the specified allowable temperature ranges. Recrystallization temperatures are selected either ranging above or below a temperature of about 95° C. depending on which polymorph product is desired. The agitation of the process mixture is carried out in the same temperature range as for the recrystallization and continues until solid/solution equilibrium has been established. The establishment of equilibrium conditions is required for these thermal processes so that thermodynamic selection of the favored polymorph dominates. The intended crystalline polymorph is then isolated, preferably by simple filtration. While filtration of the P203 polymorph is often carried out at temperatures above the 95° transition temperature; in those cases where buspirone hydrochloride's solubility in the selected liquid media is very low, cooling the mixture to room temperature prior to filtration results in negligible contamination by the P188 polymorph.

Adaptation of the above general process for polymorph production results in the following specific processes:

Process 1. Procedure for production of the low melting polymorph.

This process comprises the steps of:
(a) disrupting the crystal structure of solid buspirone hydrochloride by dissolution in a suitable liquid medium;
(b) allowing recrystallization to occur while the temperature is kept below about 95° C.;
(c) while maintaining the temperature below about 95° C., the solid buspirone hydrochloride: liquid medium mixture is agitated for a period of time sufficient to obtain solid/solution equilibrium; and
(d) separating the desired low-melting polymorph from the liquid component of the mixture.

Process 2. Procedure for production of the high melting polymorph.

This process comprises the steps of:
(a) disrupting the crystal structure of solid buspirone hydrochloride by dissolution in a suitable liquid medium;
(b) allowing recrystallization to occur while the temperature is kept above about 95° C.;
(c) while maintaining the temperature above about 95° C., the solid buspirone hydrochloride: liquid medium mixture is agitated for a period of time sufficient to obtain solid/solution equilibrium; and
(d) separating the desired high-melting polymorph from the liquid component of the mixture.

In actual practice, a solvent or solvent mixture is selected in which buspirone hydrochloride has only slight solubility below about 100° C. In these instances the solid product is composed of P203 with only negligible amounts of P188 present. This permits isolation of the solid product more conveniently at room temperature.

Certain preferred processes are those in which steps (a), (b), and (c) are combined so that the solid buspirone hydrochloride is continuously undergoing liquid medium mediated dissolution-crystallization processes at the selected temperatures until the solid buspirone hydrochloride is constituted entirely of the desired polymorph. This crystalline product is then isolated according to step (d). For these preferred processes most of the buspirone hydrochloride is suspended in the liquid medium as a solid with only minor amounts in solution. As would be expected, conversions to P203 are best carried out in liquid media comprised of higher boiling solvents or their mixtures such as xylene, butanol, xylene/cyclohexanone, nonane/cyclohexanone, and the like. The preferred range of temperatures for production of P203 is about 118° to 155° C. There is less restriction for production of P188 which occurs below 95° C., and solvents such as isopropyl alcohol, acetonitrile, and methyl ethyl ketone are examples of operable liquid media for this process. The preferred process for production of P188 employs isopropyl alcohol in the temperature range of about 25° to 60° C. Identification and semi-quantification of the polymorphs utilize micromethods such as thermomicroscopy, infrared spectroscopy and thermal analysis, especially differential scanning calorimetry (DSC) which was particularly useful in investigating the polymorphic forms and their transformations according to the instant invention.

In essence, the polymorph production processes developed for buspirone are intended to encompass any and all thermal processes which rely on thermodynamic selection of the favored polymorph above and below the transition temperature. Choice of temperatures and conversion media will affect the rates of conversion. Disclosure of these processes will be extended by reference to the specific examples which can be found hereinbelow appearing before the claims.

Another aspect of the invention is the discovery that the low-melting polymorphic modification is the energetically favored form under pharmaceutically relevant conditions and temperatures. This aspect becomes very useful for medicinal production because of the unique regulatory climate governing manufacture of pharmaceuticals. "Good manufacturing practices" as set forth and overseen by governmental drug regulatory agencies such as FDA in the U.S. require establishment of specifications for all pure drug substances and all lots of drug must be in compliance with these specifications. In the case of buspirone hydrochloride, prior art crystallization procedures which rely on kinetic control of crystallization have now been found to result in a mixture of both polymorphs, thereby causing additional expense and process time in order to produce the P203 form in order to meet NDA specifications. Additionally, lots of P203 occasionally undergo partial transformation during bulk storage thereby causing rejection of those lots for subsequent manufacture of the final pharmaceutical composition product. Not only is rework of these converted lots costly but orderly manufacture of product can be interrupted by a shortage of pure drug substance. These delays and added expenses can be eliminated by adoption of the P188 polymorph as a pure drug substance and amendment of the buspirone NDA to incorporate the P188 specifications. Utilization of the P188 polymorph will improve manufacturability of buspirone pharmaceutical products. Procedures for buspirone pharmaceutical products are given in selected references listed in the *Background of the Invention* section, supra. In particular, U.S. Pat. No. 3,717,634 and U.S. Pat. No. 4,182,763 describe pharmaceutical compounding of buspirone hydrochloride and its analogs and these patents are hereby incorporated herein by reference. The P188 polymorph can be substituted readily for P203 and maintain operability of these procedures for compounding buspirone pharmaceutical products. The P188 polymorph can also be utilized for the therapeutic purposes already shown for the P203 polymorph, such as for treatment of anxiety in patients in need of such treatment.

In summary, utilization of the newly discovered P188 polymorph of buspirone hydrochloride improves manufacturability of buspirone pharmaceutical products.

DESCRIPTION OF THE SPECIFIC EMBODIMENTS

Polymorphic modifications and the processes for their preparation and interconversion which constitute this invention will appear more fully from a consideration of the following examples which are given for the purpose of illustration only and are not to be construed as limiting invention in sphere or scope. All temperatures are understood to be in degrees C. when not specified. In addition to the elemental analysis data which are given, spectra of the product polymorphs were consistent with the assigned buspirone hydrochloride structure.

A. Preparation of P203 Buspirone Hydrochloride

EXAMPLE 1

8-[4-[4-(2-Pyrimidinyl)-1-piperazinyl]butyl]-8-azaspiro[4.5]decane-7,9-dione Hydrochloride, Buspirone HCl, Conversion of P188 polymorph to P203 polymorph in xylene.

To a 50 mL portion of xylene heated to reflux (138°-139° C.) was added 10 g (0.024 mol) of buspirone HCl low melting polymorph P188. It should be understood that mixtures of P188 and P203 may also be employed in this and any of the following examples. The suspension was stirred at 138° C. for 17 hours, then cooled spontaneously to 25° C. (see Note 1). The crystalline solid was collected on a filter and dried under reduced pressure, weight 7.5 g, m.p. 199°-200° C. (uncorr).

Note 1: In this example and others, the very limited solubility of buspirone hydrochloride in the selected solvent system results in crystallization of essentially all the product isolable from the liquid media at temperatures above the 95° transition temperature. This allows isolation of the solid product to be done under the much more convenient conditions of room temperature with only negligible contamination by the P188 polymorph.

Anal. Calc'd. for $C_{12}H_{31}N_5O_2 \cdot HCl$ C, 59.77; H, 7.65; N, 16.60; Cl, 8.40. C, 59.56; H, 7.39; N, 16.56; Cl, 8.09.

The IR (KBr) and NMR (CDCl$_3$) spectra were consistent with structure. DSC 10.68 mg sample, 10 deg/min, onset 202.89° C.

EXAMPLE 2

Buspirone HCl P188 to P203 Conversion in Xylene/cyclohexanone

A suspension of 5 g (0.0118 mol) of buspirone HCl P188 polymorph in 25 mL of xylene was heated to 138° C. under a nitrogen atmosphere. To this suspension was added 15 ml of cyclohexanone giving a clear solution. The heat was removed and the solution allowed to cool spontaneously. At 120° C. the solution became cloudy and crystallization occurred at 115° C. After cooling to 24.5° C., the solid was collected on a filter, washed with anhydrous ether, and dried under reduced pressure at 50° C. The high melting polymorph (P203) weighed 3.6 g. mp 201°-202° C.

Anal. Calc'd. for $C_{21}H_{31}N_5O_2 \cdot HCl$ C, 59.77; H, 7.65; N, 16.60; Cl, 8.40. C, 59.42; H, 7.39; N, 16.48; Cl, 8.34.

IR (KBr) and NMR (CDCl$_3$) spectra were consistent with structure. DSC, 1.45 mg sample, 10 deg/min, onset 201.3° C.

EXAMPLE 3

Buspirone HCl P188 to P203 Polymorph Conversion in Cyclohexanone/xylene.

In a 250 mL 3-necked round bottom flask fitted with a condenser, thermometer, magnetic stirrer, and nitrogen inlet tube were placed 50 mL of cyclohexanone. The solvent was heated to 155° C. and 5 g (0.0118 mol) of buspirone HCl low melting polymorph P188 was added which promptly dissolved. A stream of nitrogen gas was bubbled through the solution throughout the procedure. To this solution was added 125 mL of xylene, and the clear solution was stirred and allowed to cool slowly from 155° C. and crystallization occurred as the temperature dropped to 100°. The suspension was allowed to cool to room temperature overnight and then the white solid was collected on a filter, washed with anhydrous ether, and dried in a vacuum oven at 50° C., giving 4 g P203 polymorph, m.p. 202°-204° C.

Anal. Calc'd. for $C_{21}H_{31}N_5O_2 \cdot HCl$ C, 59.77; H, 7.65; N, 16.60; Cl, 8.40. C, 59.85: H, 7.55; N, 16.63; Cl, 8.29.

IR (KBr) and NMR (CDCl$_3$) spectra were consistent with structure. DSC, 1.62 mg sample, 10 deg/min, onset 202.1° C.

EXAMPLE 4

Buspirone HCl P188 to P203 Conversion in Nonane/Cyclohexanone

A suspension of 5 g (0.0118 mol) of buspirone HCl P188 polymorph in 25 mL of nonane was heated to reflux under a nitrogen atmosphere. To this suspension was added 40 mL of cyclohexanone giving a clear solution. The heat was removed, and the contents of the flask allowed to cool to 24° C. At 112°-117° C. crystals formed, and the resulting suspension was allowed to stir and cool to room temperature. The solid was collected on a filter, washed with several portions of anhydrous ether, and dried under reduced pressure at 50° C. giving 4.7 g of buspirone HCl P203 polymorph, m.p. 201°-203° C.

Anal. Calc'd. for $C_{21}H_{31}N_5O_2 \cdot HCl$ C, 59.77; H, 7.65; N, 16.60; Cl, 8.40. C, 59.44: H, 7.68; N, 16.48; Cl, 8.41.

IR (KBr) and NMR (CDCl$_3$) spectra were consistent with structure.

DSC, 1.63 mg sample, 10 deg/min, onset, 201.4° C.

EXAMPLE 5

Buspirone HCl P188 to P203 Conversion in 1-Butanol

A 5 g sample of buspirone HCl P188 polymorph was dissolved in 25 mL of hot 1-butanol (bp 118°) and heated at reflux under nitrogen for 1 hr. The heat was removed and the solution allowed to slowly cool and crystallize. The mixture was allowed to reach room temperature whereupon the white crystalline solid was collected on a filter, washed with several portions of dry ether, and dried under reduced pressure at 50° C. giving 3.9 g buspirone HCl P203 polymorph, m.p. 201°-203° C.

Anal. Calc'd. for $C_{21}H_{31}N_5O_2 \cdot HCl$ C, 59.77; H, 7.65; N, 16.60; Cl, 8.40. C, 59.69; H, 7.74; N, 16.87, Cl, 8.52.

IR (KBr) and NMR (CDCl$_3$) spectra were consistent with structure. DSC, 4.88 mg sample. 10 deg/min, onset, 203.3° C.

EXAMPLE 6

Larger-Scale Preparation of P203 Buspirone Hydrochloride

To a 12-L, 4-necked round flask fitted with reflux condenser, stainless steel stirring shaft and paddle, thermometer, and nitrogen inlet tube extending below the surface of the solvent, were added 2500 mL of xylene and 500 g (1.185 moles) buspirone HCl (Note 1). The suspension was heated to reflux while nitrogen gas was bubbled through the solution. When the pot temperature reached 137° C., 1500 mL of cyclohexanone was added in a thin stream (Note 2). The suspension was heated at reflux until a clear solution was obtained and no buspirone HCl remained on the walls or top of the flask. (Note 3). The heat was removed and the contents of the flask allowed to cool spontaneously. After 20 minutes, the contents of the flask cooled to 114° and crystals began to form. At 110° C., crystallization was very rapid and the mixture became thick (Note 4). The suspension was allowed to cool overnight under nitrogen atmosphere and the high melting polymorph collected on a filter, washed with 500 mL of xylene followed by 3×200 mL portions of ethyl ether. After drying in a vacuum oven to constant weight at 60° C., the buspirone HCl P203 polymorph weighed 476.5 g (95.3% recovery) m.p. 201°-202° C. DSC 10°/min., onset 199.7° C.

Anal. Calcd. for $C_{21}H_{31}N_5O_2 \cdot HCl$: C, 59.77; H, 7.65; N, 16.60; Cl, 8.40. Found: C, 59.63; H, 7.59; N, 16.45; Cl, 8.40.

Infrared and NMR spectra were consistent with structure.

Notes:
1. Either P188 or a mixture of the polymorphs may be used as starting material.
2. The pot temperature dropped to 130° during this addition.
3. A clear solution was obtained in 20–30 minutes at 136°–137° C.
4. A sample was taken and dried for melting point determination. When the melting point capillary was dropped into a melting point bath heated to 190° C., no melting occurred. This indicated complete conversion to high melting polymorph which was confirmed by differential scanning calorimetry.

B. Preparation of P188 Buspirone Hydrochloride

EXAMPLE 7

Buspirone HCl P203 to P188 Conversion in Isopropanol

A suspension of 5 g (0.118 mol) of buspirone HCl P203 polymorph in 17 mL of isopropanol was heated at 40°–42° C. for 20 hrs. The suspension was cooled to ambient temperature and the solid collected on a filter, washed with several portions of anhydrous ether, and dried under reduced pressure at 50° C. giving 4 g buspirone HCl, P188 polymorph, mp 190°–192° C. (uncorr).

Anal. Calc'd. for $C_{21}H_{31}N_5O_2 \cdot HCl$ C, 59.77; H, 7.65; N, 16.60; Cl, 8.40. C, 59.97; H, 7,49; N, 16.56; Cl, 8.17.

IR (KBr) and NMR ($CDCl_3$) spectra were consistent with structure.

DSC, 3.03 mg sample 10 deg/min, onset, 189.6° C.

EXAMPLE 8

Buspirone HCl P203 to P188 Conversion in Acetonitrile

A suspension of 5 g (0.0118 mol) of buspirone HCl P203 polymorph in 25 mL of acetonitrile was heated at reflux until a complete solution was obtained. The solution was allowed to cool at 60° C. at which temperature crystallization occurred. The reaction mixture was stirred at 60° C. for 22 hrs., then cooled at 25.5° C. The solid was collected on a filter and washed with THF. After drying under reduced pressure at 50° C., 3.8 g of buspirone HCl P188 polymorph was obtained, mp 189°–191° C.

Anal. Calc'd. for $C_{21}H_{31}N_5O_2 \cdot HCl$ C, 59.77; H, 7.65; N, 16.60; Cl, 8.40. C, 59.50; H, 7.46; N, 16.60; Cl, 8.25.

IR (KBr) and NMR ($CDCl_3$) spectra were consistent with structure.

DSC 6.55 mg sample 10 deg/min. onset 190° C.

EXAMPLE 9

Buspirone HCl P203 to P188 Conversion in Methyl Ethyl Ketone

A suspension of 5 g (0.0118 mol) of buspirone HCl P203 polymorph in 25 mL of methyl ethyl ketone was heated to reflux for one hour. The solid did not dissolve. The suspension was cooled to 60° C. and stirred at this temperature for 25 hrs. during which time the solid dissolved. After cooling to ambient temperature, the solid was collected on a filter, washed with several portions of anhydrous ether, and dried under reduced pressure at 50° C. giving 2.5 g of buspirone P188 polymorph, mp 189°–190° C.

Anal. Calc'd. for $C_{21}H_{31}N_5O_2 \cdot HCl$ C, 59.77; H, 7.65; N, 16.60; Cl, 8.40. C, 59.61; H, 7.62; N, 16.24; Cl, 8.30.

IR (KBr) and NMR ($CDCl_3$) spectra were consistent with structure.

DSC. 3.81 mg sample, 10 deg/min, onset 189.3° C.

EXAMPLE 10

Large-Scale Preparation of P188 Buspirone Hydrochloride

A 30 gallon glass reactor was charged with isopropyl alcohol (47.6 Kg), buspirone free base (17.0 Kg) and hydrochloric acid, 37% (4.4 Kg) with continuous stirring. The mixture was heated to reflux and Darco G-60 (0.85 Kg) was added. The resulting hot mixture was filtered through a filter aid bed and washed with hot isopropyl alcohol (8.0 Kg). The resulting solution was slowly cooled and allowed to stir for 24 hrs. at approximately 25° C. The resulting slurry was then cooled to 5° C. and the white solid collected and dried under vacuum at 60° C.

Yield: 16.86 Kg; 91% P188 buspirone hydrochloride.

From the foregoing examples, it would be obvious to one skilled in the chemical arts that variations in process conditions such as solvent selection, temperature, process time and the like, may be employed within the critical limits disclosed in the specification. Employing these variations does not depart from the scope of the present invention and would be considered to be equivalent processes. It should also be apparent that mixtures of the 2 polymorphic forms may be used in these processes as well as the single polymorphs themselves for conversion.

What is claimed is:

1. A process for conversion of one polymorphic crystalline form of buspirone hydrochloride into its other polymorphic crystalline form, the process comprising the steps of
    (a) disrupting the crystalline structure of either one or a mixture of the two starting polymorphic crystalline forms of buspirone hydrochloride; and
    (b) allowing recrystallization to occur under equilibrium conditions at a temperature either higher than about 95° C. if the higher melting polymorphic crystalline form of buspirone hydrochloride is desired or lower than about 95° C. if the lower melting polymorphic crystalline form of buspirone hydrochloride is desired.

2. The process of claim 1 wherein a liquid medium is employed comprising
    (a) disrupting the crystalline structure of solid buspirone hydrochloride by dissolution in the liquid medium;
    (b) allowing recrystallization to occur under equilibrium conditions at a temperature either higher than about 95° C. if the higher melting polymorphic crystalline form is desired, or lower than about 95° C. if the lower melting polymorphic crystalline form is desired; and
    (c) separating the desired polymorphic crystalline form from the liquid medium.

3. A process for selectively preparing one of the two buspirone hydrochloride polymorphic crystalline forms, the process comprising
    (a) agitating a mixture of solid buspirone hydrochloride in a liquid medium in a temperature range either higher than about 95° C., if the higher melting polymorph is desired or in a temperature range lower than about 95° C. if the lower melting polymorph is desired;
    (b) allowing solid/solution equilibrium to be established for the mixture while agitation and temperature control are employed for a time sufficient to insure that the solid buspirone hydrochloride is constituted entirely of the desired polymorphic crystalline form; and (c) separating the desired polymorphic crystalline form of buspirone hydrochloride from the liquid medium component of the mixture.

4. The process of claim 2 for production of the lower melting polymorphic crystalline form of buspirone hydrochloride which comprises the steps of (a) disrupting the crystal structure of solid buspirone hydrochloride by dissolution in a liquid medium;

(b) Allowing recrystallization to occur under equilibrium conditions while the resulting buspirone hydrochloride-liquid medium mixture is kept in a temperature range below about 95° C., and (c) separating the low-melting crystalline buspirone hydrochloride from the liquid component of the mixture.

5. The process of claim 4 wherein the temperature range is from about 40° to 80° C.

6. The process of claim 4 wherein the liquid medium is selected from the group consisting of acetonitrile, isopropanol, and methyl ethyl ketone.

7. The process of claim 3 for production of the lower melting polymorphic crystalline form of buspirone hydrochloride which comprises the steps of (a) agitating a mixture of solid buspirone hydrochloride in a liquid medium in a temperature range lower than about 95° C.;

(b) allowing solid/solution equilibrium to be established for the mixture at the temperature range lower than about 95° C. while agitation is employed for a time sufficient to insure that the solid buspirone hydrochloride is constituted entirely of the lower melting polymorph; and (c) separating the lower melting polymorphic crystalline form of buspirone hydrochloride from the liquid medium component of the mixture.

8. The process of claim 7 wherein the temperature range is from about 40° to 80° C.

9. The process of claim 7 wherein the liquid medium is selected from the group consisting of acetonitrile, isopropanol, and methyl ethyl ketone.

10. The process of claim 7 wherein the liquid medium is isopropanol and the temperature range is from about 5° C. to about 83° C.

11. The process of claim 2 for production of the higher melting polymorphic crystalline form of buspirone hydrochloride which comprises the steps of (a) disrupting the crystal structure of solid buspirone hydrochloride by dissolution in a liquid medium;

(b) allowing recrystallization to occur while the resulting buspirone hydrochloride-liquid medium mixture is kept in a temperature range above about 95° C.; and (c) separating the higher melting polymorphic crystalline form of buspirone hydrochloride from the liquid component of the mixture.

12. The process of claim 11 wherein the temperature range is from about 115° to 160° C.

13. The process of claim 11 wherein the liquid medium is selected from the group consisting of butanol, cyclohexanone, nonane, xylene, and mixtures thereof.

14. The process of claim 11 wherein the liquid medium is xylene and cyclohexanone and the temperature range is from about 110° to 140° C.

15. The process of claim 3 for production of the higher melting polymorphic crystalline form of buspirone hydrochloride which comprises the steps of (a) agitating a mixture of solid buspirone hydrochloride in a liquid medium in a temperature range higher than about 95° C.;

(b) allowing solid/solution equilibrium to be established for the mixture at the temperature range higher than about 95° C. while agitation is employed for a time sufficient to insure that the solid buspirone hydrochloride is constituted entirely of the higher melting polymorph; and (c) separating the higher melting polymorphic crystalline form of buspirone hydrochloride from the liquid medium component of the mixture.

16. The process of claim 15 wherein the temperature range is from about 115° to 160° C.

17. The process of claim 15 wherein the liquid medium is selected from the group consisting of butanol, cyclohexanone, nonane, xylene, and mixtures thereof.

* * * * *